(12) United States Patent
Tanaka et al.

(10) Patent No.: US 6,485,927 B2
(45) Date of Patent: *Nov. 26, 2002

(54) METHOD FOR QUANTITATIVELY DETERMINING BICARBONATE ION IN LIQUID AND DRY ANALYSIS DEVICE

(75) Inventors: Hideaki Tanaka, Saitama (JP); Yoshikazu Amano, Saitama (JP)

(73) Assignee: Fuji Photo Film Co., Ltd., Kanagawa (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/509,610
(22) PCT Filed: Sep. 30, 1997
(86) PCT No.: PCT/JP97/03489
§ 371 (c)(1),
(2), (4) Date: Mar. 30, 2000
(87) PCT Pub. No.: WO99/16897
PCT Pub. Date: Apr. 8, 1999

(65) Prior Publication Data
US 2002/0068311 A1 Jun. 6, 2002

(51) Int. Cl.[7] ............................ C12Q 1/32; C12Q 1/00
(52) U.S. Cl. .......................... 435/26; 435/4; 435/15; 564/80; 564/92; 564/97; 422/50; 422/68.1

(58) Field of Search .................... 435/26, 4, 15; 564/80, 92, 97; 422/50, 68.1

(56) References Cited

U.S. PATENT DOCUMENTS

| 5,514,538 A | * | 5/1996 | Evans et al. ............... 435/4 |
| 5,547,851 A | * | 8/1996 | Hattori et al. ............. 435/26 |
| 6,068,989 A | * | 5/2000 | Tanaka et al. ............ 435/26 |

FOREIGN PATENT DOCUMENTS

| JP | 4-179498 | 6/1992 |
| JP | 4-210599 | 7/1992 |

OTHER PUBLICATIONS

Clinical Chemistry, vol. 37, No. 6 (1991), pp. 915–916, "Reduced thio–nicotinamide adenine dinucleotide (t–NADH) : an alternative to measuring dehyrogenase reactions in the visible region" D.A. Nealon.

* cited by examiner

*Primary Examiner*—Louis N. Leary
(74) *Attorney, Agent, or Firm*—Reed Smith LLP

(57) ABSTRACT

This invention provides a method for the determination of bicarbonate ion existing in liquid using phosphenolpyruvate carboxylase and malate dehydrogenase as conjugate enzyme wherein thioNAD(P)H is used as substrate of malate dehydrogenase. The use of the thioNAD(P)H enables the measurement with visible light, and enables the simple and accurate determination of bicarbonate ion concentration of biological liquid sample in the clinical test.

8 Claims, 1 Drawing Sheet

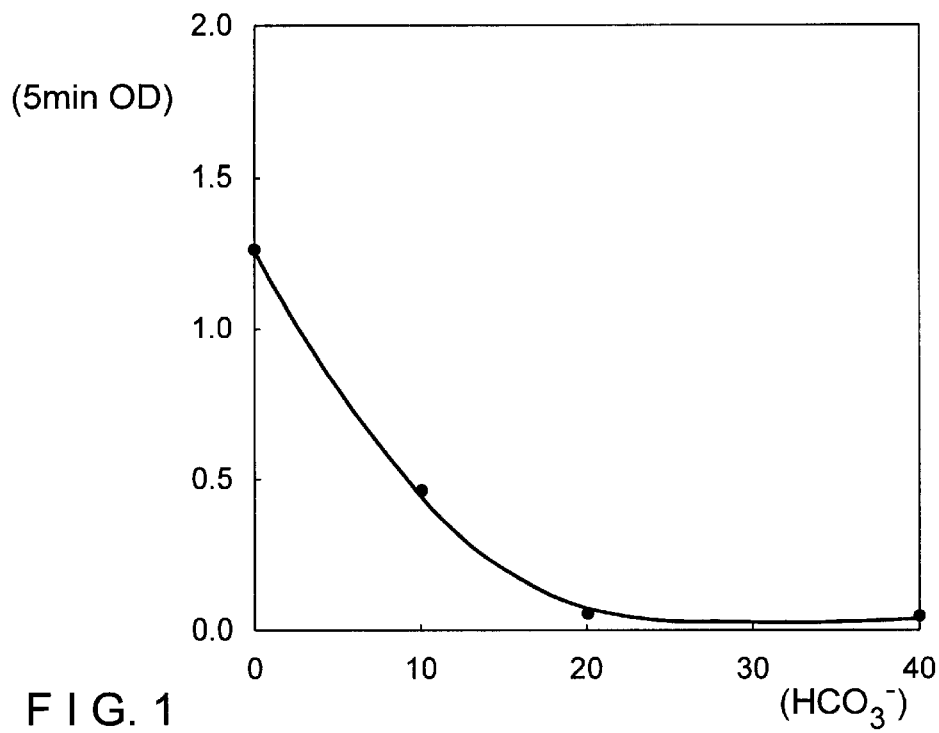
F I G. 1
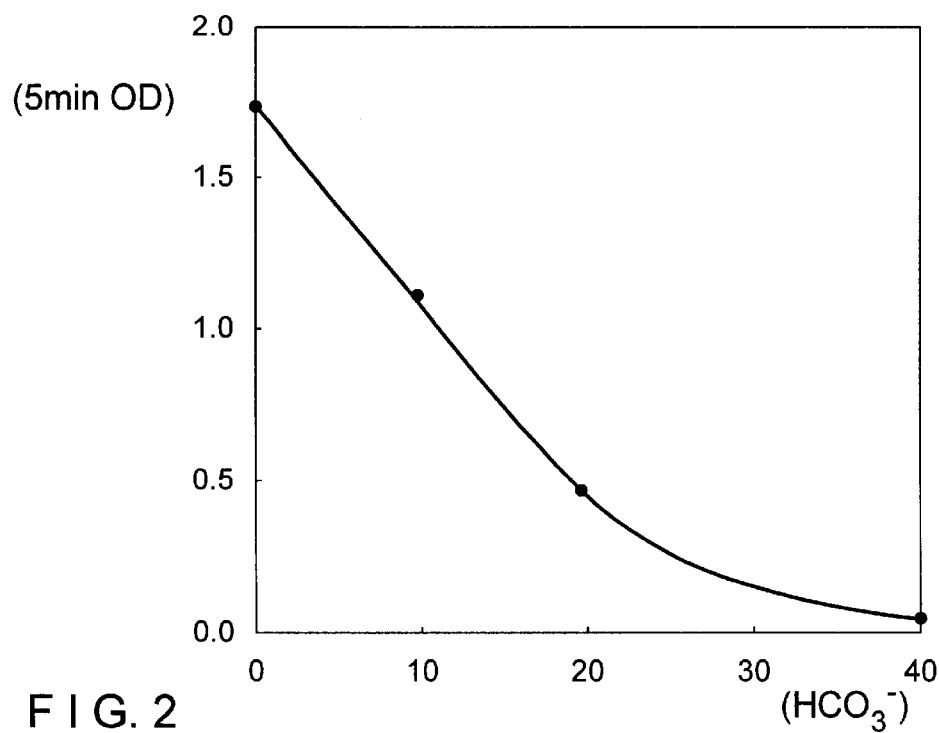
F I G. 2

METHOD FOR QUANTITATIVELY DETERMINING BICARBONATE ION IN LIQUID AND DRY ANALYSIS DEVICE

TECHNICAL FIELD

This invention concerns with a method and a dry analytical element for the determination of bicarbonate ion existing in liquid sample. In particular, the method and dry analytical element of this invention are useful in the determination of the bicarbonate ion in the liquid sample, such as blood or urine, in the clinical test where quick and accurate measurement is required.

BACKGROUND ART

A conventional method for the determination of bicarbonate ion existing in liquid sample is of measuring the partial pressure of carbonic acid in liquid and hydrogen ion concentration (pH) by using electrodes. The concentration of bicarbonate ion can be determined by calculating from the above values. However, this method is disadvantageous in the necessity of simultaneous measurement of both the partial pressure of carboxylic acid and the pH of the liquid.

Another conventional method is of utilizing the conversion of bicarbonate ion into carbon dioxide in acidic conditions, and measuring the volume of evolved carbon dioxide. In general, large-scale equipment is necessary for measuring the volume of gas precisely, and accordingly, this method is disadvantageous to the measurement of large number of samples.

In order to improve these disadvantages, some enzyme methods were developed. The enzyme method disclosed in Japanese Patent KOKAI 4-210599 utilizes the following reactions:

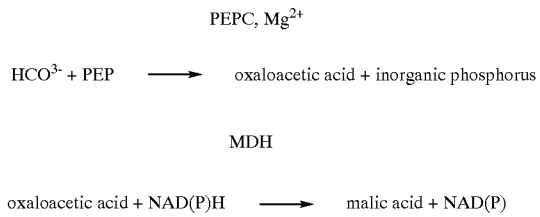

and bicarbonate ion is determined by measuring the decrease of absorption at 340 nm of NAD(P).

In the above described equation, PEPC stands for phosphenolpyruvate carboxylase, PEP stands for phosphenolpyruvic acid, MDH stands for malate dehydrogenase, NADH stands for the reduced form of nicotinamide adenine dinucleotide, NAD(P)H stands for the reduced form of nicotinamide adenine dinucleotide phosphate, and both AND and NADP stands for the oxidized form of nicotinamide adenine dinucleotide and the oxidized form of nicotinamide adenine dinucleotide phosphate respectively.

The method disclosed in Japanese Patent KOKAI 4-248997 uses phosphenolpyruvate carboxykinase instead of PEPC.

However, the above-described methods have following disadvantages:

① Since in order to measure the absorbance at 340 nm, the analyzer must be equipped with ultra-violet light source and detecting system for the ultra-violet ray. Therefore, the analyzer becomes large-scale, and expensive.

② Considering reaction rate, since the absorbance of NAD(P)H at 340 nm is of large amount, it is difficult to incorporate a necessary amount of NAD(P)H for converting the whole oxaloacetic acid produced in the above described reaction into malic acid from start. As a result, the determination range becomes narrow.

③ Although the above mentioned large absorbance can be avoided by the change of the measuring wave length to a lower absorbance range, such as 380 nm, and incorporating a sufficient amount of NAD(P)H, the measurement becomes unstable because the spectrum is not flat but oblique.

An object of the invention is to improve the above defects in the conventional determination methods of bicarbonate ion existing in liquid sample. More specifically, it is an object of this invention to provide a reaction system that enables to measure quickly, simply, and stably the bicarbonate ion in liquid using compact instrument with visual light source and sufficient substrate density. Another important object of the present invention is to provide dry analytical element to determine the bicarbonate ion in liquid.

DISCLOSURE OF INVENTION

This invention has been made in order to solve the above problems, and the object has been achieved by a method and a dry analytical element for the determination of bicarbonate ion in liquid using phosphenolpyruvate carboxylase and malate dehydrogenase as conjugate enzyme wherein thioNAD(P)H and NAD(P)H are used as substrate of malate dehydrogenase.

In the above described reaction system, reaction proceeds as follows:

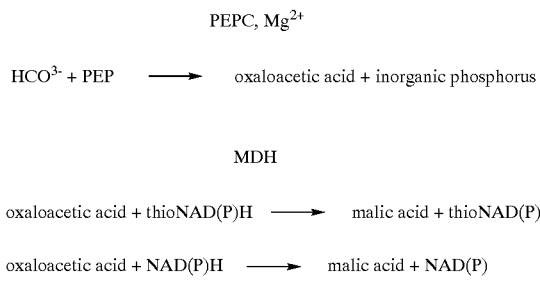

Since thioNAD(P)H has an absorption peak at 400 nm, a visible light source and detection system can be applied.

In the case where only the thioNAD(P)H is used as the substrate, the determination range becomes narrow because the absorbance of the thioNAD(P)H is as high as NAD(P)H. However, this phenomenon can be avoided maintaining the use of the visible light source and spreading the determination range by reducing the quantitative combining ratio of the bicarbonate ion to the amount of the NAD(P)H.

It is not clear what sort of competing reaction occur when bicarbonate ion contacts with thioNAD(P)H and NAD(P)H, but surprisingly the result of measurement about many specimen containing bicarbonate ion of various kinds of concentration showed reproducibility in wide determination range. Therefore, the second disadvantage described above has been solved.

BRIEF DESCRIPTION OF DRAWINGS

FIG. 1 is the graph which shows the relationship between the concentration of bicarbonate ion provided by the Example of this invention that used thio N A D H as substrate and the optical density of the reaction liquid.

FIG. 2 is the graph which shows the relationship between the concentration of bicarbonate ion provided by the Example that used the mixture of thioNADH and NADH as substrate and the optical density of the reaction liquid.

BEST MODE FOR CARRYING OUT THE INVENTION

Phosphenolpyruvate carboxylase applicable to the invention functions to produce oxaloacetic acid from phosphenolpyruvic acid, and includes EC 4.1.1.31, EC 4.1.1.32, EC 4.1.1.38 and EC 4.1.1.49. However, the presence of G D P is necessary for EC 4.1.1.32, inorganic phosphorous is necessary for EC 4.1.1.38, and ADP is necessary for EC 4.1.1.49, respectively.

As malate dehydrogenase, there are EC 1.1.1.37, EC 1.1.1.38, EC 1.1.1.39, EC 1.1.1.40, EC 1.1.1.83, and EC 1.1.99.16. The malate dehydrogenase applicable to the invention functions to produce malic acid from oxalacetic acid, and includes EC 1.1.1.37 and EC 1.1.99.16.

The measuring reagent composition of the invention also requires substrate(s) of the above two types of conjugate enzymes as well as the conjugated enzymes. The substrate(s) of phosphenolpyruvate carboxylase includes phosphenolpyruvic acid (including its derivative on which this enzyme can act). The invention is characterized by using a combination of thionicotinamide adenine dinucleotide) in reduced form (thio NADH) or thio nicotinamide adenine dinucleotide phosphate in reduced form (thioNADPH) and nicotinamide adenine dinucleotide in reduced form (NADH) or nicotinamide adenine denucleotide phosphate in reduced form (NADPH) as the substrate of malate dehydrogenase. ThioNADPH is commercially available, and for example, is supplied by Sigma Chemical Company in the U.S.A. A suitable mixing ratio (molar ratio) of thioNAD(P)H/NAD (P)H is 1/0.05 to 1/2, preferably 1/0.1 to 1/ 1, more preferably 1/0.2 to 1/0.7.

The measuring regeant composition may contain other components, such as known enzyme activators (e,g, $Mg^{2+}$), stabilizer, pH buffer, e,g. trishydroxymethlaminomethane.

A suitable amount of phosphenolpyruvic acid is about 1.5 to 10 moles, preferably about 2 to 5 moles per 1 mole bicarbonate ion. A desirable enzyme concentration is, in the case of rate assay, about 50 to 2,000 U/L, preferably about 100 to 1,000 U/L for phosphenolpyruvate carboxylase, and about 1,000 to 50,000 U/L, preferably 2,000 to 20,000 U/L for malate dehydrogenase. In the case of end point assay, a suitable phosphenolpyruvate carboxylase concentration is about 2,000 to 20,0000 U/L, preferably about 3,000 to 10,0000 U/L, and a suitable malate dehydrogenase concentration is about 2,000 to 300,000 U/L, preferably 5,000 to 200,000 U/L. A suitable amount of the sum of thio NAD (P)H and NAD(P)H is about 1 to 10 moles, preferably about 1.5 to 5 moles per one mole of $HCO^{3-}$. A suitable ratio (activity ratio) of phosphenolpyruvate carboxylase/malate dehydrogenase is about 1 to 20, preferably about 1 to 10.

The reaction is carried out at a pH of about 6 to 10, preferably around the optimum pH±1 of both enzymes, at 20 to 40° C., generally at room temperature, for 1 to 15 minutes. The measurement may be determined using the rate assay method or the end point method.

The measuring reagent composition of this invention can be used for the dry analysis as well as the wet analysis.

A preferable analytical element used in dry analysis comprises three or more layer construction composed of a water-impermeable support and at least two water permeable layers.

As a support, a water-impermeable light-transmissive support used for conventionally know dry analytical element can be applied. Typical water-impermeable light transmissive supports are, a transparent film or sheet made of polyethylene terephlate, polycarbonate of bisphenol A, polystyrene, cellulose ester such as cellulose diacetate, cellulose triacetate, and cellulose acetate proprianate. The thickness of the support is usually in the range of from about 50 μm to 1 mm, preferably from about 80 μm to about 300 μm.

The support may be provided with an undercoating layer on its surface in order to strengthen the adhesion between the support and the reagent layer laminated thereon. Instead of the undercoating layer, the surface of the support may be treated by physical or chemical activation for the enhancement of adhesion.

The water permeable layer are regeant layer, light shielding layer, adhesive layer, spreading layer, water absorption layer, that will be described in the followings:

On the support, the reagent layer is provided (directly or through other layer(s) such as undercoating layer or so). The reagent layer is a water-absorptive water permeable layer wherein at least a part of the aforementioned reagent composition is dispersed substantially uniformly in a hydrophilic polymer binder.

The hydrophilic polymer which can be used as binder of the reagent layer is generally natural or synthetic hydrophilic polymer having a swelling ratio in the range of from about 150% to about 2,000%, preferably from about 250% to about 1,500%, at 30° C. As examples of such hydrophilic polymer, there are gelatins (e.g. acid-processed gelatin or deionization gelatin, etc.), gelatin derivatives (e.g. phthalic gelatin, hydroxyacrylate graft gelatin, etc.), agarose, pullulan, pullulan derivative, polyacrylamide, polyvinylalchol, polyvinylpyrrolidone, and so on that are disclosed in Japanese Patent KOKAI 58-171864 or 60-108753.

The reagent layer may be a cross linked (cured) layer to a certain degree by adding a cross linking agent. As examples of the cross linking agent, there are known vinyl sulfonyl cross linking agents such as 1,2-bis (vinylsulfonyl acetamide) ethane and bis (vinylsulfonylmethyl) ether, aldehydes, etc., for gelatin, aldehydes, epoxy compounds having 2 glycidyl groups, and the like for methallyl alcohol copolymer.

A suitable dry thickness of the reagent layer is in the range of from about 1 μm to about 100 μm, preferably from about 3 μm to about 30 μm . It is suitable for the reagent layer to be substantially transparent.

A light-shielding layer can optionally be provided on the reagent layer. The light shielding layer is water-transmissive or water-permeable layer where fine particles with light shielding property of light absorption and/or light reflection are dispersedly maintained by the hydrophilic polymer binder having a little film formation ability. The light shielding layer blocks the color of the sample spotted on the spreading layer described later, particularly the red components of hemoglobin in the case of whole blood samples, when a detectable change, such as color change or coloration, produced in the reagent layer is measured from the side of the light-transmissive support by reflection photometry. This layer also functions as a light-reflecting layer or a background layer. As examples of light reflective fine particles, there are titanium dioxide particles (being microcrystalline fine grains in rutile type, anatase type or brookite type having a grain size of about 0.1 μm to 1.2 μm), barium sulfate particles, aluminum particles or micro flakes. As examples of light absorbing fine particles, there are carbon black, gas black, carbon micro beads, and so on. Among these light-shielding fine particles, titanium dioxide fine particles, barium sulfate particles are desirable. In particular, titanium dioxide particles in anatase type are the most preferable light shielding fine particles.

Typical hydrophilic property polymer binders having film formation ability are weak hydrophilic regenerated cellulose, cellulose acetate, etc., together with similar hydrophilic polymer as hydrophilic polymer used for the manufacture of the above-mentioned reagent layer. Preferable hydrophilic polymers are gelatins, gelatin derivatives, and polyacrylamide. A known curing agent (cross linking agent) may be added to the gelatin, or a gelatin derivative. Applying an aqueous solution of a hydrophilic polymer wherein light shielding fine particles are dispersed on the reagent layer by the well-known coating method, followed by drying may form the light-shielding layer. Instead of providing the light-shielding layer, the light-shielding fine particles may be incorporated in a spreading layer that will be described later.

An adhesive layer, together with any other optional layer may be provided on the reagent layer in order to adhere to laminate the spreading layer described later on it directly or optically through a light-shielding.

The adhesive layer is preferably composed of a hydrophilic polymer and it can join the spreading layer thereby to integrate respective layers while it is moistened or swelled by absorbing water. As examples of the hydrophilic polymer that can be applied for the production of the adhesive layer, there are the same hydrophilic polymers already described as those that can be applied for the production of the reagent layer. Among these polymers, gelatins, gelatin derivatives, polyacrylamide, etc., are preferable. A suitable dry thickness of the adhesive layer is, in general, in the range of from about 0.5 $\mu$m to about 20 $\mu$m, preferably from about 1 $\mu$m to about 10 $\mu$m.

The adhesion layer may also be provided on other layer(s) to improve adhesive force between other layers, in addition to the reagent layer. The adhesive layers can be formed by applying aqueous hydrophilic polymer solution, to which a surfactant or the like is optionally added, onto the support, or onto the reagent layer by well known coating method or another well known method.

The porous spreading layer may be a woven fabric spreading layer disclosed in Japanese Patent KOKAI 55-164356, 57-66359, etc., such as plain weave including broadcloth, and poplin, a knitted fabric spreading layer disclosed in Japanese Patent KOKAI 60-222769, etc., such as tricot, double tricot, or Milanese, a spreading layer made of a woven fabric or knitted fabric etched by etching solution disclosed in Japanese Patent KOKAI 1-172753, a spreading layer organic polymer fiber pulp containing paper disclosed in Japanese Patent KOKAI 57-148250, a membrane filter (blushed polymer layer) disclosed in Patent KOKOKU 53-21677 and U.S. Pat. No. 3,992,158, a continuous micro spaces-containing porous layers where polymer particulates, glass particulates or diatomaceous earth are dispersed in a hydrophilic polymer binder, or a continuous containing-containing porous layer where polymer particulates are joined so as to contact with each other at a point by using a polymer adhesive which does not swell in water (three-dimensional lattice structure layer).

Physical activation treatment represented by glow discharge treatment or corona discharge treatment disclosed in Japanese Patent KOKAI 57-66359 may be conducted on at least one surface of woven cloth, knitted cloth or mined paper used as the porous spreading layer in order to increase the adhesion force between the surface of the support and the coated layer. The woven cloth, knitted cloth or mined paper may be treated with degreasing by rinsing in water, or with hydrophilic treatment with a surfactant or a hydrophilic polymer disclosed in Japanese Patent KOKAI 55-164356, 57-66359, and so on. By providing the fabric or paper with one or more of the above described treatment, the fabric or paper is rendered hydrophilic, and the adhesive force between the surface of the support and the undermost coated layer that contacts with the surface can be strengthened.

Regarding the multilayer analytical element of this invention, a water absorption layer may be provided between the support and the reagent layer. The absorption layer is mainly composed of a hydrophilic polymer that absorbs water to swell, and it absorbs the water of aqueous liquid sample that reaches the surface of this layer. In the case of whole blood specimen, it accelerates permeation of blood plasma component into the reagent layer. The hydrophilic polymer usable for the water absorption layer can be selected from the polymer mentioned as usable regarding the reagent layer. Preferable hydrophilic polymers usable for the water absorption layer are, in general, gelatin, a gelatin derivative, polyacrylamide, and polyvinyl alcohol, particularly the above-mentioned gelatins and deionized gelatin. The best selection is the same gelatin as those used for the reagent layer. The dry thickness of the water absorption layer is in the range of from about 3 $\mu$m to 100 $\mu$m, preferably from about 5 $\mu$m to of about 30 $\mu$m. The coating amount of the water absorption layer is in the range of from about 3 g/m$^2$ to about 100 g/m$^2$, preferably from about 5 g/m$^2$ to about 30 g/m$^2$. By incorporating a pH buffer, known basic polymer or the like that will be described later, into the water absorption layer, practical pH in the case of analytical operation can be adjusted. Moreover, a known mordant, polymer mordant, etc., may be incorporated into the water absorption layer.

The reagent composition can be incorporated into the reagent layer or any other one or more layers. For example, it can be incorporated into the reagent layer or the spreading layer. All of the reagent composition can be incorporated into the reagent layer. In this case, components reacting with each other are incorporated separately, and the latter component is incorporated so that reaction does not proceed before measurement by, for example, dispersing the component in alcohol and then applying the dispersion.

EXAMPLE 1

The following solutions were prepared:

| | |
|---|---|
| 1) Enzyme solution | |
| Tris buffer | 75 mM(pH8) |
| PEPC(EC4.1.1.31) | 3 U/ml |
| MDH (EC1.1.1.37) | 30 U/ml |
| Mg$^{2+}$ | 19.8 mM |
| 2) Substrate solution | |
| Tris buffer | 75 mM(pH8) |
| PEP | 6.75 mM |
| thioNADH | 0.45 mM |
| 3) HCO$^{3-}$ solution | |
| 0 | mM |
| 10 | mM |
| 20 | mM |
| 40 | mM |

At 37° C., 20 μl of the above 3) solution was put in each cell, 2 ml of the above 1) solution and subsequently 1 ml of the above 2) solution were added to the cell. The absorbance at 40 Onm of this mixture was measured for five minutes, and a calibration curve was prepared using the measured absorbance after five minutes. The results are shown in FIG. 1.

From the above results, it can be seen that the determination of bicarbonate ion is possible at a measuring wavelength of 400 nm.

EXAMPLE 2

Instead of the above 2) substrate solution, the following 4) substrate solution was prepared:
4) Substrate solution

| Trisbuffer | 75 mM(pH8) |
| PEP | 6.75 mM |
| thioNADH | 0.45 mM |
| NADH | 0.23 mM |

Hereafter, bicarbonate ion was determined in the manner similar to the Example 1. The calibration curve thus obtained is shown in FIG. 2.

From the results, it can be seen that determination range is considerably widened by the coexistence of NADH in the substrate solution.

EXAMPLE 3

An aqueous solution was coated onto a clear PET film support of 180 μm in thickness and then dried so as to form the following coating amounts:

| thioNADH | 2 g/m$^2$ |
| MDH(EC1.1.1.37) | 4000 U/m$^2$ |
| Trisbuffer | 4.85 g/m$^2$ |
| Polyoxyethylenenonylphenylether | 0.25 g/m$^2$ |
| Galatin | 10 g/m$^2$ |

An aqueous solution was coated onto the above-described coated layer and then dried so as to form the following coating amounts:

| PDP | 6 g/m$^2$ |
| PEPC(EC4.1.1.31) | 4500 U/m$^2$ |
| MgCl2 | 3 g/m$^2$ |
| Trisbuffer | 4.85 g/m$^2$ |
| Polyoxyethylenenonylphenylether | 0.25 g/m$^2$ |
| Gelatin | 10 g/m$^2$ |
| Titanium dioxide | 3.65 g/m$^2$ |

On this layer, polyester knitted fabric was laminated and an aqueous solution containing polyvinyl alcohol and surfactant was coated in order to control the spreading of sample solution.

The analytical element thus prepared was cut into pieces of about 1.3×1.4 cm, and set in a mount having an opening of a diameter of 12 mm to complete an analytical element.

Each 10 μl of the sample 3) solution prepared in Example 1 was spotted onto 4 pieces of the analytical element, and the measurement was carried out similar to the Example 1. Then, similar results as Example 1 were obtained.

EXAMPLE 4

An aqueous solution was coated onto a clear PET film support of 180 μm in thickness and then dried so as to form the following coating amounts:

| thioNADH | 2 g/m$^2$ |
| NADH | 1 g/m$^2$ |
| MDH(EC1.1.1.37) | 4000 U/m$^2$ |
| Trisbuffer | 4.85 g/m$^2$ |
| Polyoxyethylenenonylphenylether | 0.25 g/m$^2$ |
| Gelatin | 10 g/m$^2$ |

Hereinafter, another analytical elements were prepared similar to the Example 3, and then similar measurements were carried out.

The results showed good performance of the invention similar to the Example 2.

Industrial Field of Utilization

This invention provides quick, accurate, and simple method for the determination of bicarbonate ion existing in biological liquid sample such as, in particular, blood, urine and so on.

What is claimed is:

1. A method for the determination of bicarbonate ion in a liquid comprising:

adding a reagent composition which comprises phosphenolpyruvate carboxylase and malate dehydrogenase as conjugate enzyme, thioNAD(P)H and NAD(P)H as a substrate of malate dehydrogenase and pH buffer; and measuring absorption in the visible region to determine presence of bicarbonate ion.

2. The method of claim 1, wherein the molar ratio of thioNAD(P)H/NAD(P)H is 1/0.05–1/2.

3. A method for the determination of bicarbonate ion in a liquid comprising:

adding a reagent composition which comprises phosphenolpyruvate carboxylase and malate dehydrogenase as a conjugate enzyme, thioNAD(P)H and NAD(P)H as a substrate of malate dehydrogenase and an enzyme activator; and measuring absorption in the visible region to determine presence of bicarbonate ion.

4. The method of claim 3, wherein the molar ratio of thioNAD(P)H/NAD(P)H is 1/0.05–1/2.

5. A dry analytical element for the determination of bicarbonate ion in a liquid comprising at least two water-permeable layers laminated onto a water-impermeable support, wherein at least one of the water-permeable layers is a porous spreading layer and the water permeable layers as a whole contain a reagent composition comprising phosphenolpyruvate carboxylase. malate dehydrogenase, thioNAD(P)H and NAD(P)H.

6. The dry analytical element of claim 5, wherein the reagent composition further comprises a pH buffer.

7. The dry analytical element of claim 5, wherein the reagent composition further comprises an enzyme activator.

8. A dry analytical element for the determination of bicarbonate ion in liquid comprising at least two water-permeable layers laminated onto a water-impermeable support, wherein the water-permeable layers as a whole contain phosphenolpyruvate carboxylase, malate dehydrogenase, thioNAD(P)H is 1/0.05–1/2.

* * * * *